United States Patent [19]
Grün et al.

[11] Patent Number: 5,928,931
[45] Date of Patent: Jul. 27, 1999

[54] ISOLATION, PURIFICATION AND CLONING OF RETINOL DEHYDRATASE

[75] Inventors: Felix Grün, Stamford, Conn.; Jochen Buck; Ulrich Hammerling, both of New York, N.Y.

[73] Assignees: Cornell Research Foundation, Inc., Ithaca; Sloan-Ketterin Institute for Cancer Research, New York, both of N.Y.

[21] Appl. No.: 08/852,481

[22] Filed: May 7, 1997

Related U.S. Application Data

[60] Provisional application No. 60/017,178, May 9, 1996.
[51] Int. Cl.[6] .............................. C12N 15/60; C12N 9/88; C12N 1/21; C12N 15/63
[52] U.S. Cl. ................... 435/252.3; 435/232; 435/320.1; 435/71.2; 536/23.2
[58] Field of Search ........................... 536/23.2; 435/232, 435/320.1, 252.3, 71.2

[56] References Cited

FOREIGN PATENT DOCUMENTS

WO 94/20081   9/1994   European Pat. Off. .

OTHER PUBLICATIONS

Buck et al., "Anhydroretinol: A Naturally Occurring Inhibitor of Lymphocyte Physiology," *J. Exp. Med.*, 178:675–80 (1993).

Bhat et al., "Retinoid Metabolism in Spontaneously Transformed Mouse Fibroblasts (Balb/c 3T12–3 Cells): Enzymatic Conversion of Retinol to Anhydroretinol," *Journal of Lipid Research*, 20:357–62 (1979).

Buck et al., "Intracellular Signaling by 14–Hydroxy–4, 14–*Retro*–Retinol," *Science*, 254:1654–56 (1991).

Derguini et al., "Spectroscopic Studies of Anhydroretinol, and Endogenous Mammalian and Insect Retro –Retinoid," *Angew. Chem. Int. Ed. Engl.*, 33(18):1837–39 (1994).

Coughtrie et al., "Sulfation of Endogenous Compounds and Xenobiotics–Interactions and Function in Health and Disease," *Chemico–Biological Interactions*, 92:247–56 (1994).

Yamazoe et al., "Structural Similarity and Diversity of Sulfotransferases," *Chemico–Biological Interactions*, 92:107–17 (1994).

*Primary Examiner*—Rebecca E. Prouty
*Attorney, Agent, or Firm*—Nixon, Hargrave, Devans & Doyle LLP

[57] ABSTRACT

The present invention relates to retinol dehydratase, the enzyme which synthesizes the retro-retinoid anhydroretinol in the *Spodoptera frugiperda* insect cell line Sf-21, as well as the DNA molecule encoding that enzyme. The DNA molecule can be incorporated in a DNA expression system and a host for recombinant production of anhydroretinol dehydratase. The isolated retinol dehydratase protein or polypeptide of the present invention can be combined with a pharmaceutically-acceptable carrier or used alone for administration to mammals, particularly humans, for preventing cell growth and/or uncontrolled cell growth in cells which are growth dependent on retinol and/or 14 hydroxy-4, 14-retro-retinol.

12 Claims, 10 Drawing Sheets

```
Nuc.Pos.                                                                                                                    AA Res.
       1  acaaccattactgaacagtcgtcagcgcaacaactagtatttgcattgtgtagacaacatagttatcacagtgat
      81  agaaaATGGAGAAACAACAGGATTTGCCATTCCCTTACGAGTTTAGGGAGCTTAACCCCGAAGAAGATAAATTGGTTAAA
           M  E  K  Q  Q  D  L  P  F  P  Y  E  F  R  E  L  N  P  E  E  D  K  L  V  K        25
     161  GCCAATTTAGGCGCGGTTCCCCACAACTACTGTGAAACTGGGCCTAAAGGCTACATGTGTACAGACCCTACTTGAAAGA
          (A  N  L  G  A  F  P  T  T  Y  V  K) L  G  P  K  G  Y  M  V  Y  R  P  Y  L  K  D   52
     241  TGCGGCGAATATCTACAACATGCCTCTAAGACCTGACGTGTTCGTTGCAGTTATCAAGATCAGGAACGACAATGA
           A  A  N  I  Y  N  M  P  L  R  P  T  D  V  F  V  A  S  Y  Q  R (S  G  T  M        78
     321  CTCAAGAACTAGTTTGGCTAATTGAAAACGACTTGAATTTCGAAGCTGCAAAAACATACATGTCCCTCCGCTACATTTAT
           T  Q  E  L  V  W  L  I  E  N  D  L  N  F  E  A  A  K) T  Y  M  S  L  R (Y  I  Y   105
     401  CTTGACGGCTTCATGATCTACGACCCGGAGAAGCAAGAAGAATATAACGACATATTACCAAATCCAGAAAACCTTGATAT
           L  D  G  F  M  I  Y  D  P  E  K  Q  E  E  Y  N  D  I  L  P) N  P  E  N  L  D  M   132
     481  GGAAAGGTATTTAGGATTGCTAGAATACTTTAGTCGTCCAGGGAGCTCATTGCTCGCTGCAGTGCCACCGACAGAGAAAA
           E  R  Y  L  G  L  L  E  Y  F  S  R  P  G  S  S  L  L  A  A  V  P  P  T  E  K      158
     561  GATTTGTGAAGACCCACTTGCCTTTGTCCTTGATGCCTCCAATATGTTGGATACTGTGAAGATGTGTACCTGGCTCGA
           R  F  V  K  T  H  L  P  L  S  L  M  P  P  N  M  L  D  T  V  K  M  V  Y  L  A  R   185
     641  GACCCTAGAGACGTGGCGGTTGTTCACCGTGGCCTATATACGCTACACCATATTTCGAGCACGTCAAGGAAGCTTCAAAGA
           D  P  R  D  V  A  V  S  S  F  H  H  A  R  L  L  Y  L  L  N  K  Q  S  N  F  K  D   212
     721  TTTCTGGGAAATGTTCACCGTGGCCTATATACGCTACACCATATTTCGAGCACGTCAAGGAAGCTTGGGCAAAGAGAC
           F  W  E  M  F  H  R  G  L  Y  T  L  T  P  Y  F  F  E  H  V  K  E  A  W  A  K  R   238
     801  ATGATCCGAACATGCTGTTTTTGATCGAGGAACAAATTCAGCGCCTCTGCGAACACCTGAATTTCGAATTCAAAAACAATGGCGC
           H  D  P  N  M  L  F  Y  E  D  Y  L  K  D  L  P  G  C  I  A  R  I  A  D  F          265
     881  TTGGGCAAGAAGTTGAGTGAGGAACAAATTCAGCGCCTCTGCGAACACCTGAATTTCGAATTCAAAAACAATGGCGC
           L  G  K  K  L  S  E  E  Q  I  Q  R  L  C  E  H  L  N  F  E  K  F  K  N  N  G  A   292
     961  TGTCAATATGGAGGACTACAGGGAGATTGGGAATACTCGCTGACGGGGAGCATTCATTAGAAAAGGTAAAGCAGGATGCT
           V  N  M  E  D  Y  R  E  I  G  I  L  A  D  G  E  H  F  I  R  K  G  K  A  G  C      318
    1041  GGCGCGACTACTTCGACGAGGAGGAGATGACGAAACAAGCTGAGAAATGGATCAAGGACAACCTGAAGGATACTGATCTGCGC
           W  R  D  Y  F  D  E  E  M  T  K  Q  A  E  K  W  I  K  D  N  L  K  D  T  D  L  R   345
    1121  TACCCAAATATGGAATTAtaatcaactgtaaattataataagcataagtaaattaagaacgtctacgttctataatg
           Y  P  N  M  E  L
    1201  tctatcggatttatgatattatttagaaaataataatcaatacaataatattttatagtaatataaggtat
    1281  acaattattttttcttgcttgtcataaaactaccctagtcgcaggcactaagtatatattaactccattgcctaaagtta
    1361  tttcatagcaatgaaattgtctattgctgcttgctagcgtgtcttaatattgtacctgttgattacctaatatttt
    1441  ctttattctgactttactgtagtagataatgattgatatattaccttctctattattccagactataaattaattggtaac
    1521  cttatttttacctttgtaaggaaataaactcacgtatttttat
```

FIG. 4

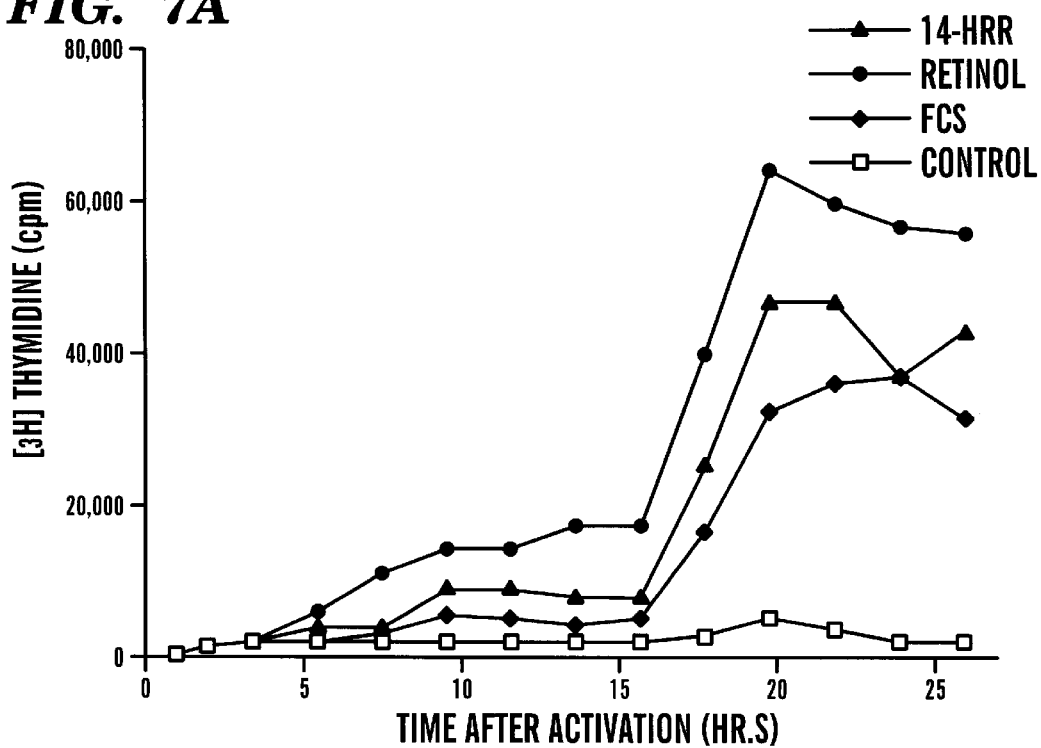
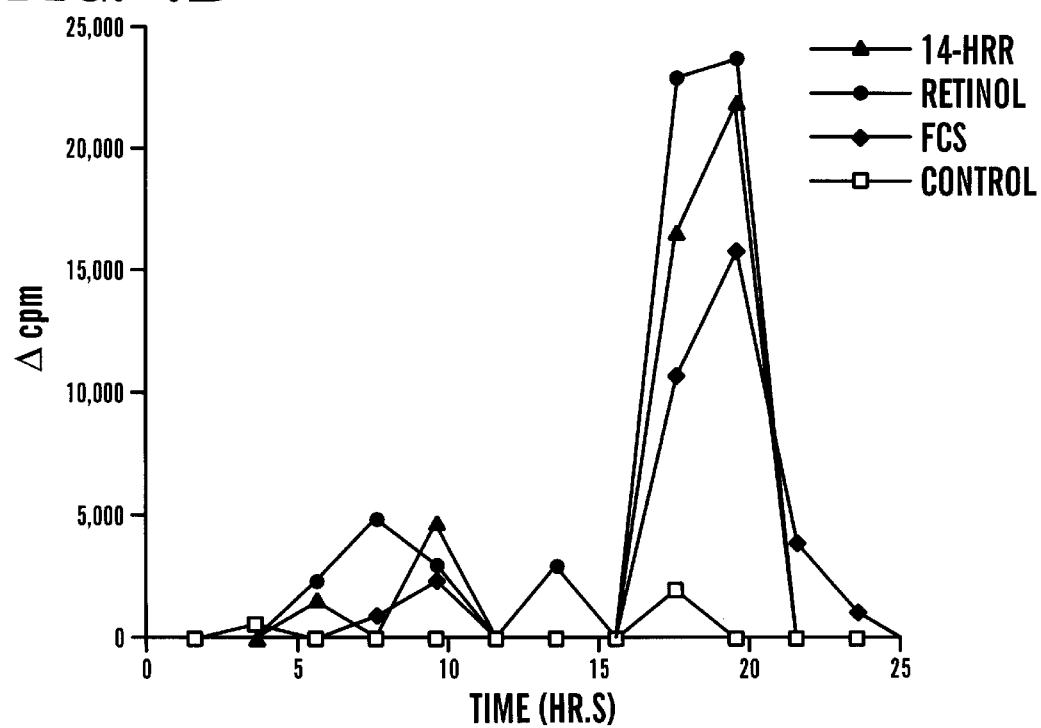

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1564 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ACAACCATTA CTGAACAGTC GTCAGCGCAA CAACTAGTAT TTTGCATTTA TGGTGTAGAC      60

AACATAGTTA TCACAGTGAT AGAAAATGGA GAAACAACAG GATTTGCCAT TCCCTTACGA     120

GTTTAGGGAG CTTAACCCCG AAGAAGATAA ATTGGTTAAA GCCAATTTAG GCGCGTTCCC     180

CACAACCTAC GTGAAACTGG GGCCTAAAGG CTACATGGTG TACAGACCCT ACTTGAAAGA     240

TGCGGCGAAT ATCTACAACA TGCCTCTAAG ACCTACAGAC GTGTTCGTTG CCAGTTATCA     300

ACGATCAGGA ACGACAATGA CTCAAGAACT AGTTTGGCTA ATTGAAAACG ACTTGAATTT     360

CGAAGCTGCA AAAACATACA TGTCCCTCCG CTACATTTAT CTTGACGGCT TCATGATCTA     420

CGACCCGGAG AAGCAAGAAG AATATAACGA CATATTACCA AATCCAGAAA ACCTTGATAT     480

GGAAAGGTAT TTAGGATTGC TAGAATACTT TAGTCGTCCA GGGAGCTCAT TGCTCGCTGC     540

AGTGCCACCG ACAGAGAAAA GATTTGTGAA GACCCACTTG CCTTTGTCCT TGATGCCTCC     600

CAATATGTTG GATACTGTGA AGATGGTGTA CCTGGCTCGA GACCCTAGAG ACGTGGCGGT     660

GTCCAGCTTC CACCACGCCC GGTTATTGTA TTTGCTGAAT AAGCAGAGCA ACTTCAAAGA     720

TTTCTGGGAA ATGTTTCACC GTGGCCTATA TACGCTGACA CCATATTTCG AGCACGTCAA     780

GGAAGCTTGG GCAAAGAGAC ATGATCCGAA CATGCTGTTT TTGTTTTACG AAGACTACTT     840

AAAGGACTTA CCAGGCTGCA TTGCACGTAT CGCTGACTTC TTGGGCAAGA AGTTGAGTGA     900

GGAACAAATT CAGCGCCTCT GCGAACACCT GAATTTCGAA AAGTTCAAAA ACAATGGCGC     960

TGTCAATATG GAGGACTACA GGGAAATTGG AATACTCGCT GACGGGGAGC ATTTCATTAG    1020

AAAAGGTAAA GCAGGATGCT GGCGCGACTA CTTCGACGAG GAGATGACGA AACAAGCTGA    1080

GAAATGGATC AAGGACAACC TGAAGGATAC TGATCTGCGC TACCCAAATA TGGAATTATA    1140
```

-continued

```
ATCAACTGTA AAATTATATA ATAAGCATAA GTAAATTAAG AACGTCTACG TTCTATAATG      1200

TCTATCGGAT TTATGGATAT TATTTAGAAA AATAGAATTA ATCAATACAA TAACAATATT      1260

TTTATAGTAA TATAAGGTAT ACAATTATTT TTTCTTGCTT GTCATAAAAC TACCCTAGTC      1320

GCAGGCACTA AGTATAAATT AACTCCATTG CCTAAAGTTA TTTTCATAGC AATGAAATTG      1380

TCTATTGCTG CTTGCTAGCG TGTCTTTAAT ATTGTACCTG TTGGATTTAC CTAATATTTT      1440

CTTTATTCTG ACTTTACTGT AGTAGATAAT GGATTTGATA TTAACCTTCT ATTATTCCAG      1500

ACTATAAATT AATTGGTAAC CTTATTTTTA CCTTTTGTAA GGAAATAAAC TCACGTATTT      1560

TTAT                                                                  1564
```

(2) INFORMATION FOR SEQ ID NO:2:

(i) SEQUENCE CHARACTERISTICS:
        (A) LENGTH: 350 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu Lys Gln Gln Asp Leu Pro Phe Pro Tyr Glu Phe Arg Glu Leu
1               5                   10                  15

Asn Pro Glu Asp Lys Leu Val Lys Ala Asn Leu Gly Ala Phe Pro Thr
            20                  25                  30

Thr Tyr Val Lys Leu Gly Pro Lys Gly Tyr Met Val Tyr Arg Pro Tyr
        35                  40                  45

Leu Lys Asp Ala Ala Asn Ile Tyr Asn Met Pro Leu Arg Pro Thr Asp
50                  55                  60

Val Phe Val Ala Ser Tyr Gln Arg Ser Gly Thr Thr Met Thr Gln Glu
65                  70                  75                  80

Leu Val Trp Leu Ile Glu Asn Asp Leu Asn Phe Glu Ala Ala Lys Thr
                85                  90                  95

Tyr Met Ser Leu Arg Tyr Ile Tyr Leu Asp Gly Phe Met Ile Tyr Asp
            100                 105                 110

Pro Glu Lys Gln Glu Glu Tyr Asn Asp Ile Leu Pro Asn Pro Glu Asn
        115                 120                 125

Leu Asp Met Glu Arg Tyr Leu Gly Leu Leu Glu Tyr Phe Ser Arg Pro
130                 135                 140

Gly Ser Ser Leu Leu Ala Ala Val Pro Pro Thr Glu Lys Arg Phe Val
145                 150                 155                 160

Lys Thr His Leu Pro Leu Ser Leu Met Pro Pro Asn Met Leu Asp Thr
                165                 170                 175

Val Lys Met Val Tyr Leu Ala Arg Asp Pro Arg Asp Val Ala Val Ser
            180                 185                 190

Ser Phe His His Ala Arg Leu Leu Tyr Leu Leu Asn Lys Gln Ser Asn
        195                 200                 205

Phe Lys Asp Phe Trp Glu Met Phe His Arg Gly Leu Tyr Thr Leu Thr
210                 215                 220

Pro Tyr Phe Glu His Val Lys Glu Ala Trp Ala Lys Arg His Asp Pro
225                 230                 235                 240

Asn Met Leu Phe Leu Phe Tyr Glu Asp Tyr Leu Lys Asp Leu Pro Gly
                245                 250                 255

Cys Ile Ala Arg Ile Ala Asp Phe Leu Gly Lys Lys Leu Ser Glu Glu
            260                 265                 270
```

```
Gln Ile Gln Arg Leu Cys Glu His Leu Asn Phe Glu Lys Phe Lys Asn
        275                 280                 285

Asn Gly Ala Val Asn Met Glu Asp Tyr Arg Glu Ile Gly Ile Leu Ala
        290                 295                 300

Asp Gly Glu His Phe Ile Arg Lys Gly Lys Ala Gly Cys Trp Arg Asp
305                 310                 315                 320

Tyr Phe Asp Glu Glu Met Thr Lys Gln Ala Glu Lys Trp Ile Lys Asp
            325                 330                 335

Asn Leu Lys Asp Thr Asp Leu Arg Tyr Pro Asn Met Glu Leu
            340                 345                 350
```

ISOLATION, PURIFICATION AND CLONING OF RETINOL DEHYDRATASE

This application claims the benefit of U.S. Provisional patent application Ser. No. 60/017,178, filed May 9, 1996.

This invention was developed under NIH Grant Nos. DK-48022 and CA-49933.

FIELD OF THE INVENTION

The present invention relates to the isolation, purification, and cloning of retinol dehydratase.

BACKGROUND OF THE INVENTION

The diverse family of isoprenoid lipids, of which the retinoids represent one class, has been used in cellular signaling pathways since the beginning of multicellular life. Processes in vertebrates as diverse as growth, vision, and reproduction are "retinoid" dependent. *The Retinoids*, Vol. 2, eds. Spom, M. B., Roberts, A. B., & Goodman, D. S., pp. 289–286 [Academic, Orlando 1984]. Retinoids are a group of compounds consisting of retinol (i.e. Vitamin A) and natural and synthetic derivatives thereof.

Various metabolic derivatives of retinol have been identified. Retinoic acid has been found to be crucial for normal pattern formation during embryogenesis and in the regulation of the differentiation of a variety of cell types (Gudas L. J.,*J. Biol. Chem.*, 2679:15399–402 (1994)), 11-cis retinal in vision (Wald, G. , *Science*, 162:230–32 (1968)) or 9-cis and all-trans retinoic acid for differentiation of a number of cellular systems (*The Retinoids*, Vol. 2, eds. Sporn, M. B., Roberts, A. B., & Goodman, D. S., pp. 289–286 [Academic, Orlando 1984]).

Furthermore, retinoic acid receptors are members of an ancient superfamily of nuclear receptors, some of which respond to other isoprenoid derivatives, e.g. steroids (Evans, R. M., *Science*, 240:889–95 (1988) and Green et al., *Trends, in Genet.*, 4:309–14 (1988)), vitamin D (McDonnell et al., *Science*, 235:1214–17 (1987)) and ecdysone (Koelle et al., *Cell*, 67:59–77 (1991)).

The general mechanism of action of retinoids presumably is connected with their specific binding proteins including nuclear receptor molecules that are involved in transcriptional regulation (Evans, R. M., *Science*, 240:889–95 (1985) and Green et al., *Trends in Genet.*, 4:309–14 (1988)). Retro-retinoids are characterized by a planar ring-to-tail configuration, rigidly enforced by the rearrangement of the carbon double bond system to fix the hexenyl ring by a double bond to the polyene tail. The first of the natural retro-retinoids to be discovered, 14-hydroxy-4,14-retro-retinol ("14-HRR") plays a role in the regulation of lymphocyte proliferation. Garbe et al.,*J. Exp. Med.*, 176:109–17 (1992) and Buck et al., *Science*, 254:1654–56 (1991).

The hydrocarbon anhydroretinol, first detected in 1939 in fish liver oils (Embree, N. D., *J. Biol Chem.*, 128:187–198 (1939)), is structurally related to 14-HRR and was, therefore, tested for its effects on B cell proliferation. B lymphocytes, although retinol-dependent, do not use retinoic acid as mediator. Retinol is metabolized by B lymphocytes and other cell lines to optically active 14-HRR. It is this compound that mediates the growth control. Buck et al., *Science*, 254:1654–56 (1991).

Anhydroretinol, although a structural analog of 14-HRR, has been shown to be an antagonist to 14-HRR and not an aid to B cell proliferation. However, it reversibly inhibits retinol- and 14-HRR-dependent effects and blocks B lymphocyte proliferation as well as activation of resting T lymphocytes. Buck et al., *J Exp. Med.*, 178:675–80 (1993).

It has been shown that spontaneously transformed mouse fibroblasts (Balb/c 3T12–13 cells) cultured in vitro in the presence of trans retinol synthesized the hydrocarbon anhydroretinol and metabolite-310 from retinol. Moreover, incubation of metabolite-310 with the 3T12 microsomes yielded anhydroretinol by these cells, suggesting that metabolite-310 is an intermediate in the synthesis of anhydroretinol by these cells i.e., retinol is enzymatically converted to anhydroretinol. Bhat et al., *J. Lipid Res.*, 20:357–62 (1979). Furthermore, anhydroretinol's antagonism to 14-HHR suggests that this retro-retinoid might function as a ligand for cytoplasmic or nuclear receptors. Derguini et al., *Angew. Chem. Int. Ed. Engl.*, 33(18):1837–39 (1994).

WO 94/20081 to Hammerling et al. discloses anhydroretinol and derivatives thereof, for inhibiting the growth of cells, treating a subject having a disease characterized by an uncontrolled growth of cells, and blocking an immune response.

SUMMARY OF THE INVENTION

The present invention relates to an isolated DNA molecule encoding the protein or polypeptide retinol dehydratase, as well as isolated proteins or polypeptides encoded by the isolated DNA molecule.

The DNA molecules can be inserted as heterologous DNA in an expression vector forming a recombinant DNA expression system for producing the retinol dehydratase protein or polypeptide. Likewise, the heterologous DNA, usually inserted in an expression vector to form a recombinant DNA expression system, can be incorporated in a cell to achieve this objective.

The isolated protein or polypeptide of the present invention can be combined with a pharmaceutically-acceptable carrier or used alone for administration to cells under conditions effective to antagonize cell growth or cell proliferation mediated by 14-hydroxy-4,14-retro-retinol ("14-HRR") or retinol. Alternatively, such antagonism can be achieved by providing a host cell containing the DNA molecule of the present invention with other cells, expressing the protein or polypeptide of the present invention in the presence of retinol and converting the retinol in other cells to anhydroretinol with the expressed protein or polypeptide.

The DNA molecule of the present invention, the protein or polypeptide of the present invention, or the antibodies or binding portions thereof raised against the proteins or polypeptides can also be utilized in a method for detection of cells expressing retinol dehydratase. In this manner, the proteins or polypeptides or antibodies (including binding portions thereof and probes) are utilized as an antigen. In these procedures, using an assay system, a sample is contacted with the antigen and any reaction indicates that cells expressing retinol dehydratase are present in the sample.

In addition, cells expressing retinol dehydratase can be detected in a sample by providing the nucleotide sequence encoding retinol dehydratase or a fragment thereof, as a probe in a nucleic acid hybridization assay or a gene amplification detection procedure (e.g., using a polymerase chain reaction procedure). A sample is then contacted with the probe. Any reaction with the probe is detected so that the presence of the cells assayed for in the sample is indicated.

Isolation of the DNA molecule of the present invention which encodes for retinol dehydratase constitutes a significant advance in the treatment of cells that are growth-dependent on 14-hydroxy-4,14-retro-retinol or retinol, because it provides the basis for a pharmaceutical carrier or agent to treat a patient having a disease characterized by an uncontrolled or unwanted growth of cells. Such a system can be used to induce not only humoral immunity but cell-mediated immunity. The isolated protein or polypeptide encoded by the DNA molecule of the invention can be produced at high levels using conventional recombinant DNA technology.

In diagnostic applications, the protein or polypeptide of the present invention permit rapid determination of whether a particular individual is infected with a disease characterized by an uncontrolled or unwanted growth of cells. Moreover, such detection can be carried out without requiring an examination of the individual being tested for an antibody response.

Furthermore, the protein or polypeptide or DNA molecules of the present invention can be utilized in conjunction with gene therapy regimens.

BRIEF DESCRIPTION OF THE DRAWINGS

FIG. 4 shows the cDNA sequence and deduced amino acid sequence of retinol dehydratase (bracketed residues represent tryptic peptides T34 (A-K: res. 26–37), T66 (S-K: res. 74–96), and T56 (Y-P: res. 103–125); and highly conserved sulfotransferase sequence motifs implicated for a 3'-phosphosadenosine 5'-phosphosulfate ("PAPS") binding site are underlined).

In FIG. 6(a), one to four day serum-starved cells activated by serum, retinol, 14-HRR, and the peptide growth factors epidermal growth factor ("EGF") and platelet derived growth factor ("PDGF") are shown. FIG. 6(B) shows dose-response curves of retinol, 14-HRR, and fetal calf serum on four day serum-starved NIH 3T3 cells. NIH 3T3 cells were grown to confluence in Dulbecco's minimal essential medium ("DMEM") containing 10% fetal calf serum in 96-well microliter plates. All media were supplemented with 2 mM glutamine and 100 U/ml of penicillin/streptomycin. Cells were washed once with phosphate-buffered saline solution and incubated for one to four days in 200 $\mu$l/well of DMEM media/0.1% fetal calf serum ("starvation media"). On the indicated day, starvation media was replaced with 200 $\mu$l/well of insulin, transferrin, linoleic acid, bovine serum albumin ("ITLB") media, with or without fetal calf serum, retinoids, or peptide growth factors at the indicated concentrations. ITLB media is RPMI media (Gibco BRL, Grand Island, N.Y.) containing dilapidates bovine serum albumin (1.2 mg/ml), linoleic acid (10$^{-6}$M), bovine insulin (5 $\mu$g/ml), and transferrin (5 $\mu$g/ml). [$^3$H] thymidine (1.2 $\mu$Ci per well) was added at the beginning of the experiment, and the thymidine incorporation was determined after 24 h. The data represent the mean of triplicate measurements and standard deviations ("SD") were $\leq$17%. Recombinant PDGF (B/B) and EGF were purchased from Sigma Chemical Company or Boehringer Mannheim Corporation. Anhydroretinol was synthesized by acid catalyzed dehydration of all-trans-retinol. Embree, *J. Biol. Chem.* 128:187–98 (1939) and Derguini, et al., *Angew. Chem. Int. Ed. Engl.* 33:1839–41 (1994), which are hereby incorporated by reference. All-trans-14-hydroxy-4,14-retro-retinol was synthesized as described. Derguini, et al., *J. Biochem.* 33:623–28 (1994), which is hereby incorporated by reference.

FIG. 7 shows that retinoid and serum activated resting NIH 3T3 cells enter S phase in parallel. Cells starved for 4 days in DMEM/0.1% fetal calf serum were activated with 5% fetal calf serum, 2 $\mu$M retinol, or 2 $\mu$M 14-HRR, and the cumulative thymidine incorporation was determined at the indicated time points. $\Delta$cpm corresponds to the increase in [$^3$H]thymidine incorporation in the two hour period before the time point shown. This method is described in FIG. 6. The data in FIG. 7 represents the mean of quadruplicate measurements and SDs were $\leq$15%.

DETAILED DESCRIPTION OF THE INVENTION

Figure 1A:
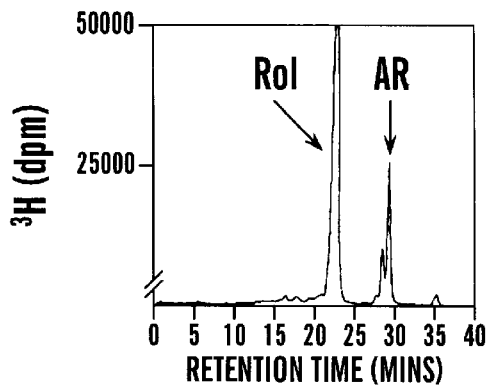
FIGS. 1A–1F are graphs showing metabolic labeling for retinol dehydratase activity in *Spodoptera frugiperda* cells and subcellular fractions ((A) $10^7$ *Spodoptera frugiperda* Sf-21 cells; (B) Sf-9 cells incubated with $\mu$Ci $^3$H-retinol in Grace's insect cell media; (C) retinol dehydratase activity localized to 100,000×g supernatant of Sf-21 sonicates; (D) activity in microsomal fractions; (E) dialyzed Sf-21 cytosolic supernatant cells; and (F) dialyzed Sf-21 cytosolic supernatant complementary with non-dialyzed Sf-9 cytosolic supernatant).

Anhydroretinol ("AR") is the major metabolite of retinol in the *Spodoptera frugiperda* insect cell line Sf-21. The substrate for AR is free retinol. The present invention relates, inter alia, to the isolation, purification, and cloning of retinol dehydratase, the enzyme which synthesizes the retro-retinoid anhydroretinol in the *Spodoptera frugiperda* insect cell line Sf-21. The cloned cDNA has GenBank accession number: U28654, which is hereby incorporated by reference.

One aspect of the present invention relates to an isolated DNA molecule encoding retinol dehydratase, the cytosolic enzyme which synthesizes anhydroretinol in the *Spodoptera frugiperda* insect cell line Sf-21. This DNA molecule encodes an open reading frame for full length retinol dehydratase. Retinol dehydratase has a molecular weight of about 41 to 42 kDa, particularly, 41.5 kDa, and a nucleotide sequence corresponding to SEQ. ID. No. 1 as follows:

| | | | | | | |
|---|---|---|---|---|---|---|
| ACAACCATTA | CTGAACAGTC | GTCAGCGCAA | CAACTAGTAT | TTTGCATTTA | TGGTGTAGAC | 60 |
| AACATAGTTA | TCACAGTGAT | AGAAAATGGA | GAAACAACAG | GATTTGCCAT | TCCCTTACGA | 120 |
| GTTTAGGGAG | CTTAACCCCG | AAGAAGATAA | ATTGGTTAAA | GCCAATTTAG | GCGCGTTCCC | 180 |
| CACAACCTAC | GTGAAACTGG | GGCCTAAAGG | CTACATGGTG | TACAGACCCT | ACTTGAAAGA | 240 |
| TGCGGCGAAT | ATCTACAACA | TGCCTCTAAG | ACCTACAGAC | GTGTTCGTTG | CCAGTTATCA | 300 |
| ACGATCAGGA | ACGACAATGA | CTCAAGAACT | AGTTTGGCTA | ATTGAAAACG | ACTTGAATTT | 360 |
| CGAAGCTGCA | AAAACATACA | TGTCCCTCCG | CTACATTTAT | CTTGACGGCT | TCATGATCTA | 420 |
| CGACCCGGAG | AAGCAAGAAG | AATATAACGA | CATATTACCA | AATCCAGAAA | ACCTTGATAT | 480 |
| GGAAAGGTAT | TTAGGATTGC | TAGAATACTT | TAGTCGTCCA | GGGAGCTCAT | TGCTCGCTGC | 540 |
| AGTGCCACCG | ACAGAGAAAA | GATTTGTGAA | GACCCACTTG | CCTTTGTCCT | TGATGCCTCC | 600 |
| CAATATGTTG | GATACTGTGA | AGATGGTGTA | CCTGGCTCGA | GACCCTAGAG | ACGTGGCGGT | 660 |
| GTCCAGCTTC | CACCACGCCC | GGTTATTGTA | TTTGCTGAAT | AAGCAGAGCA | ACTTCAAAGA | 720 |
| TTTCTGGGAA | ATGTTTCACC | GTGGCCTATTA | TACGCTGACA | CCATATTTCG | AGCACGTCAA | 780 |
| GGAAGCTTGG | GCAAAGAGAC | ATGATCCGAA | CATGCTGTTT | TTGTTTTACG | AAGACTACTT | 840 |
| AAAGGACTTA | CCAGGCTGCA | TTGCACGTAT | CGCTGACTTC | TTGGGCAAGA | AGTTGAGTGA | 900 |
| GGAACAAATT | CAGCGCCTCT | GCGAACACCT | GAATTTCGAA | AAGTTCAAAA | ACAATGGCGC | 960 |
| TGTCAATATG | GAGGACTACA | GGGAAATTGG | AATACTCGCT | GACGGGGAGC | ATTTCATTAG | 1020 |
| AAAAGGTAAA | GCAGGATGCT | GGCGCGACTA | CTTCGACGAG | GAGATGACGA | AACAAGCTGA | 1080 |
| GAAATGGATC | AAGGACAACC | TGAAGGATAC | TGATCTGCGC | TACCCAAATA | TGGAATTATA | 1140 |
| ATCAACTGTA | AAATTATATA | ATAAGCATAA | GTAAATTAAG | AACGTCTACG | TTCTATAATG | 1200 |
| TCTATCGGAT | TTATGGATAT | TATTTAGAAA | AATAGAATTA | ATCAATACAA | TAACAATATT | 1260 |
| TTTATAGTAA | TATAAGGTAT | ACAATTATTT | TTTCTTGCTT | GTCATAAAAC | TACCCTAGTC | 1320 |
| GCAGGCACTA | AGTATAAATT | AACTCCATTG | CCTAAAGTTA | TTTTCATAGC | AATGAAATTG | 1380 |
| TCTATTGCTG | CTTGCTAGCG | TGTCTTTAAT | ATTGTACCTG | TTGGATTTAC | CTAATATTTT | 1440 |
| CTTTATTCTG | ACTTTACTGT | AGTAGATAAT | GGATTTGATA | TTAACCTTCT | ATTATTCCAG | 1500 |
| ACTATAAATT | AATTGGTAAC | CTTATTTTTA | CCTTTTGTAA | GGAAATAAAC | TCACGTATTT | 1560 |
| TTAT | | | | | | 1564 |

The nucleotide sequence corresponding to SEQ. ID. No. 1 encodes the following deduced amino acid sequence (SEQ. ID. No. 2):

```
Met Glu Lys Gln Gln Asp Leu Pro Phe Pro Tyr Glu Phe Arg Glu Leu
1               5                   10                  15

Asn Pro Glu Asp Lys Leu Val Lys Ala Asn Leu Gly Ala Phe Pro Thr
            20                  25                  30

Thr Tyr Val Lys Leu Gly Pro Lys Gly Tyr Met Val Tyr Arg Pro Tyr
            35                  40                  45

Leu Lys Asp Ala Ala Asn Ile Tyr Asn Met Pro Leu Arg Pro Thr Asp
            50                  55                  60

Val Phe Val Ala Ser Tyr Gln Arg Ser Gly Thr Thr Met Thr Gln Glu
65                      70                  75                  80

Leu Val Trp Leu Ile Glu Asn Asp Leu Asn Phe Glu Ala Ala Lys Thr
                    85                  90                  95

Tyr Met Ser Leu Arg Tyr Ile Tyr Leu Asp Gly Phe Met Ile Tyr Asp
                100                 105                 110

Pro Glu Lys Gln Glu Glu Tyr Asn Asp Ile Leu Pro Asn Pro Glu Asn
            115                 120                 125

Leu Asp Met glu Arg Tyr Leu Gly Leu Leu Glu Tyr Phe Ser Arg Pro
            130                 135                 140
```

```
Gly Ser Ser Leu Leu Ala Ala Val Pro Pro Thr Glu Lys Arg Phe Val
145                 150                 155                 160

Lys Thr His Leu Pro Leu Ser Leu Met Pro Pro Asn Met Leu Asp Thr
                165                 170                 175

Val Lys Met Val Tyr Leu Ala Arg Asp Pro Arg Asp Val Ala Val Ser
            180                 185                 190

Ser Phe His His Ala Arg Leu Leu Tyr Leu Leu Asn Lys Gln Ser Asn
            195                 200                 205

Phe Lys Asp Phe Trp Glu Met Phe His Arg Gly Leu Tyr Thr leu Thr
        210                 215                 220

Pro Tyr Phe Glu His Val Lys Glu Ala Trp Ala Lys Arg His Asp Pro
225                 230                 235                 240

Asn Met Leu Phe Leu Phe Tyr Glu Asp Tyr Leu Lys Asp Leu Pro Gly
                245                 250                 255

Cys Ile Ala Arg Ile Ala Asp Phe Leu Gly Lys Lys Leu Ser Glu Glu
            260                 265                 270

Gln Ile Gln Arg Leu Cys Glu His Leu Asn Phe Glu Lys Phe Lys Asn
            275                 280                 285

Asn Gly Ala Val Asn Met Glu Asp Tyr Arg Glu Ile Gly Ile Leu Ala
        290                 295                 300

Asp Gly Glu His Phe Ile Arg Lys Gly Lys Ala Gly Cys Trp Arg Asp
305                 310                 315                 320

Tyr Phe Asp Glu Glu Met Thr Lys Gln Ala Glu Lys Trp Ile Lys Asp
                325                 330                 335

Asn Leu Lys Asp Thr Asp Leu Arg Tyr Pro Asn Met Glu Leu
            340                 345                 350
```

The anhydroretinol dehydratase of the present invention is capable of synthesizing anhydroretinol using retinol as a substrate at physiological intracellular concentrations. In such applications, the retinol has a $K_m$ value of about $0.6 \times 10^{-9}$ to $2.0 \times 10^{-9}$. Further, the anhydroretinol dehydratase enzyme of the present invention has about 20 to 26% amino acid sequence homology to sulfotransferases.

Also encompassed by the present invention are fragments of the above DNA molecules and the proteins or polypeptides they encode. Suitable fragments are constructed by using appropriate restriction sites, revealed by inspection of the DNA molecule's sequence, to: (i) insert an interposon (Felly, et al., "Interposon Mutagenesis of Soil and Water Bacteria: A Family of DNA Fragments Designed for in vitro Insertion Mutagenesis of Gram-negative Bacteria," *Gene* 52:147–15 (1987), which is hereby incorporated by reference) such that truncated forms of the polypeptides or proteins of the present invention, that lack various amounts of the C-terminus, can be produced or (ii) delete various internal portions of the protein. Alteratively, the sequence can be used to amplify any portion of the coding region, such that it can be cloned into a vector supplying both transcription and translation start signals.

Variants may also (or alteratively) be made by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The protein or polypeptide of the present invention (i.e., retinol dehydratase) is preferably produced in purified form by conventional techniques. For instance, see Example 5 infra. To isolate the protein or polypeptide retinol dehydratase, the host cell carrying a recombinant plasmid is propagated, homogenized, and the homogenate is centrifuged to remove cellular/bacterial debris. The supernatant is then subjected to sequential ammonium sulfate precipitation. The fraction containing the protein of the present invention is subjected to gel filtration in an appropriately sized dextran or polyacrylamide column to separate the proteins. If necessary, the protein fraction may be further purified by HPLC.

The DNA molecules of the invention encoding retinol dehydratase can be incorporated in cells using conventional recombinant DNA technology. Generally, this involves inserting the selected DNA molecules into an expression system to which that DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences. U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eucaryotic cells grown in tissue culture. Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gtl1, gt WES.TB, Charon 4, and plasmid vectors such as pBR322, pBR325, pACYCI77, pACYCI84, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et. al., "Use of T7 RNA Polymerase to Direct Expression of Cloned Genes," vol 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Clonings: A Laboratory Manual*, Cold Springs Laboratory, Cold Springs Harbor, N.Y. (1982), which is hereby incorporated by reference.

A variety of host-vector systems may be utilized to express the protein-encoding sequence(s) of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus) . The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation). Transcription of DNA is dependent upon the presence of a promotor which is a DNA sequence that directs the binding of RNA polymerase and thereby promotes mRNA synthesis. The DNA sequences of eucaryotic promotors differ from those of prokaryotic promoters. Furthermore, eucaryotic promoters and accompanying genetic signals may not be recognized in or may not function in a prokaryotic system, and, further, prokaryotic promoters are not recognized and do not function in eucaryotic cells.

Similarly, translation of mRNA in prokaryotes depends upon the presence of the proper prokaryotic signals which differ from those of eucaryotes. Efficient translation of mRNA in prokaryotes requires a ribosome binding site called the Shine-Dalgarno sequence on the mRNA. This sequence is a short nucleotide sequence of mRNA that is located before the start codon, usually AUG, which encodes the amino-terminal methionine of the protein. The Shine-Dalgarno sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (i.e. isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno sequence about 7–9 bases 5' to the initiation codon (ATG) to provide a ribosome binding site. Thus, any Shine Dalgarno-ATG combination that can be utilized by host cell ribosomes may be employed. Additionally, any Shine-Dalgarno-ATG combination produced by recombinant DNA or other techniques involving incorporation of synthetic nucleotides may be used.

Once the DNA molecule of the present invention has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, and the like.

In view of the present invention's determination of nucleotide sequences which encode for the enzyme retinol dehydratase, it is possible to treat a patient having a disease characterized by an uncontrolled or unwanted growth of cells that are growth dependent on retinol or 14-HRR. In this regard, anhydroretinol has been shown to be an antagonist to 14-HRR and does not aid B cell proliferation. That is, anhydroretinol reversibly inhibits retinol- and 14-HRR-dependent effects and blocks B lymphocyte proliferation as well as activation of resting T lymphocytes. With this information and the above-described recombinant DNA technology, a wide array of therapeutic agents and diagnostic procedures are possible for, respectively, treating and detecting cells that are growth-dependent on 14-HRR or retinol, such as, for example, tumor cells, activated T cells, transformed B cells, and myeloid cells. Examples of tumor cells include, but are not limited to, T-cell lymphomas, T-cell leukemias, B-cell lymphomas, B-cell leukemias, myeloid leukemia cells, and cancer cells such as breast cancer cells.

For example, an effective cell growth controlling amount of the proteins or polypeptides of the present invention can be administered alone or in combination with a pharmaceutically acceptable carrier to cells under conditions effective to antagonize cell growth or cell proliferation mediated by retinol. Alternatively, cell growth or cell proliferation mediated by retinol is antagonized by providing a host cell containing the DNA molecule encoding retinol dehydratase with a promoter causing that enzyme to be expressed when retinol is present. The expressed enzyme is used to convert retinol in other cells to anhydroretinol. Such cells can be in culture or in a mammal.

In the practice of the invention, the retinol dehydratase is effective to suppress either the patient's cellular immune response or humoral immune response. The cellular immune response to which the retinol dehydratase is effective is the patient's cellular immune response which is mediated by the subject's $CD4^+$ T cells or by $CD8^+$ T cells. A target of the humoral immune response to which the present invention is effective is the patient's antibody-forming B lymphocytes. Diseases which are characterized by such a humoral immune response in a patient are well known to those skilled in the art. Examples of such diseases include, but are not limited to, graft versus host disease, psoriasis, allergic reactions, and autoimmune diseases. The present invention is also effective against immune responses due to transplantation into the patient, such as, kidney, heart, or lung transplantation and bone marrow transplantation. Examples of allergic reactions in a subject are well known to those in the art and include allergic reactions due to external as well as internal stimuli. Examples of external stimuli include poison ivy, poison oak, poison sumac, or insect venom. Examples of internal stimuli include administration of other medicaments, allergic reactions to beverages and food, and allergic reactions resulting from the internalization in a subject of airborne allergens such as smoke or pollen. Examples of autoimmune diseases against which the present invention is effective include rheumatoid arthritis, nephrosis, thyroiditis, and diabetes mellitus.

The pharmaceutically-acceptable agents or carriers of this invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The solid unit dosage forms can be of the conventional type. The solid form can be a capsule, such as an ordinary gelatin type containing the proteins or peptides of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents such as, cornstarch, potato starch, or alginic acid, and a lubricant like stearic acid or magnesium stearate.

The proteins or polypeptides of the present invention can also be administered in injectable dosages by solution or suspension of these materials in a physiologically acceptable diluent with a pharmaceutical carrier. Such carriers include sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions.

For use as aerosols, the proteins or polypeptides of the present invention in solution or suspension can be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

In the practice of the present invention, the amount of isolated protein or polypeptide incorporated into the pharmaceutically-acceptable carrier can vary widely. Factors considered when determining the precise amount are well known to those skilled in the art. Examples of such factors include, but are not limited to, the subject being treated, the specific pharmaceutical carrier and route of administration being employed and the frequency with which the composition is to be administered.

The protein or polypeptide of the present invention can be used to raise monoclonal or polyclonal antibodies.

Monoclonal antibody production may be effected by techniques which are well-known in the art. Basically, the process involves first obtaining immune cells (lymphocytes) from the spleen of a mammal (e.g., mouse) which has been previously immunized with the antigen of interest (i.e, the protein or peptide of the present invention) either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. The virus is carried in appropriate solutions or adjuvants. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain preimmune serum. The antigens can be injected at a total volume of 100 $\mu$l per site at six different sites. Each injected material will contain synthetic surfactant adjuvant pluronic polyols or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbitol 150 mg/Kg IV. This and other procedures for raising polyclonal antibodies are disclosed in E. Harlow, et. al., editors, *Antibodies: A Laboratory Manual* (1988), which is hereby incorporated by reference.

In addition to whole antibodies, the present invention encompasses use of binding fragments or portions of such antibodies. Such binding fragments or portions include Fab fragments, F(ab')$_2$ fragments, and Fv fragments. Such fragments or portions can be made by conventional procedures, such as proteolytic fragmentation procedures, as described in J. Goding, *Monoclonal Antibodies: Principles and Practice*, pp. 98–118 (N.Y. Academic Press 1983), which is hereby incorporated by reference.

Alternatively, the process of the present invention can utilize probes found either in nature or prepared synthetically by recombinant DNA procedures or other biological procedures. Suitable probes are molecules which bind to the protein or polypeptide of the present invention. Such probes can be in the form of proteins, peptides, lectins, or nucleic acids.

In yet another aspect of the present invention, the protein or polypeptide of the present invention can be used as an antigen in diagnostic assays for the detection of unwanted cell growth in body fluids. Such techniques permit detection in a sample of the following tissue or body fluids: blood, spinal fluid, sputum, pleural fluids, urine, bronchial alveolor lavage, lymph nodes, bone marrow, or other biopsied materials.

In one embodiment, the assay system has a sandwich or competitive format. Examples of suitable assays include an enzyme-linked immunosorbent assay, a radioimmunoassay, a gel diffusion precipitan reaction assay, an immunodiffusion assay, an agglutination assay, a fluorescent immunoassay, a protein A immunoassay, or an immunoelectrophoresis assay.

In an alternative diagnostic embodiment of the present invention, the nucleotide sequences of the isolated DNA molecules of the present invention may be used as a probe in nucleic acid hybridization assays for the detection of unwanted cells in various patient body fluids. The nucleotide sequences of the present invention may be used in any nucleic acid hybridization assay system known in the art, including, but not limited to, Southern blots (Southern, *J. Mol. Biol.*, 98: 503–17 (1975)(which discloses hybridization in 2×SSC (i.e. 0.15M NaCl, 0.015 sodium citrate), 40% formamide at 40° C.); Northern blots (Thomas et al., *Proc. Nat'l Acad. Sci. USA* 77:5201–05 (1980)); Colony blots (Grunstein et al., *Proc. Nat'l Acad. Sci. USA*, 72:3961–65 (1975), which are hereby incorporated by reference). Alternatively, the isolated DNA molecules of the present invention can be used in a gene amplification detection procedure (e.g., a polymerase chain reaction). See H. A. Erlich et. al., "Recent Advances in the Polymerase Chain Reaction," *Science* 252:1643–51 (1991), which is hereby incorporated by reference.

The following examples and preparations describe the manner and process of making and using the present invention, but are not to be construed as limiting.

EXAMPLES

Example 1
Metabolic Labelling For Retinol Dehydratase Activity $10^7$ *Spodoplera frugiperda* Sf-21 cells or Sf-9 cells were incubated with 1 μCi$^3$H-retinol in Grace's insect cell media for 6 hours. Delipidated and radiolabelled retinoid metabolites were analyzed by radiomatic detection after separation by HPLC. Retinol was eluted at 21 minutes, and anhydroretinol isomers were eluted between 26.5 and 29 minutes.

Figure 1B:
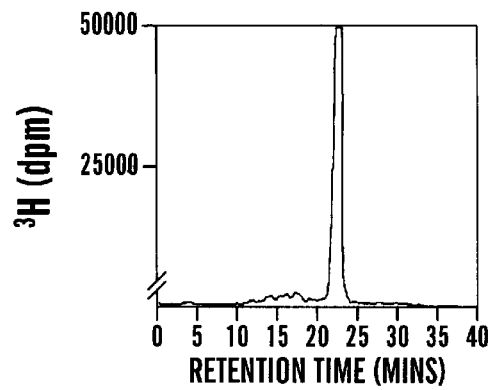

Radiolabelling Sf-21 cultures with [$^3$H]-retinol resulted in one predominant metabolite as shown in FIG. 1A. The retinol derivative was identified as the all-trans and cis-isomers of anhydroretinol by co-elution with synthetic standards on reverse phase HPLC and the characteristic vibronic fine structure in the UV/Vis absorption spectrum (maxima at 270, 348, 368, and 390 nm), as described by Derguini et al., *Angew. Che. Int. Ed. Engl.*, 33:1839–41 (1994), which is hereby incorporated by reference. Cellular production of AR was time dependent but could be disrupted by 2% glutaraldehyde fixation, 0.1% sodium azide treatment or heat inactivation at 55° C. for 15 minutes (respectively causing 90%, 96%, and 99% inhibition compared to controls). These data strongly suggested that the synthesis of AR was an energy and protein dependent process. Incubations of $10^7$ Sf-21 cells for as short as 10 minutes gave detectable quantities of [$^3$H]-AR, while no AR production was detectable in Sf-9 cultures, as shown in FIG. 1B, even with extended incubation times of up to 24 hours. Enzymatic production of AR had also previously been reported to occur in spontaneously transformed mouse fibroblasts as described by Bhat et al., *Journal of Lipid Research*, 20:357–62 (1979), which is hereby incorporated by reference.

Figure 1C:
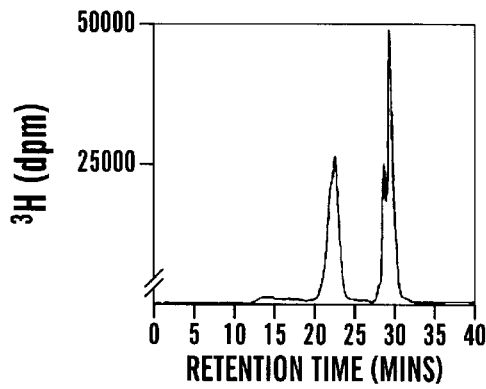
Figure 1D:
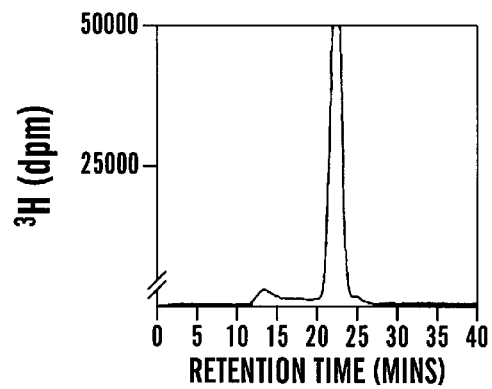
Figure 1E:
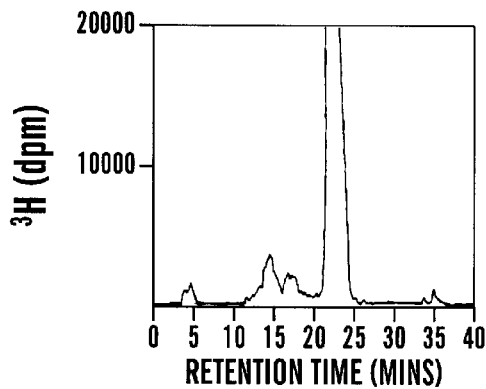
Figure 1F:
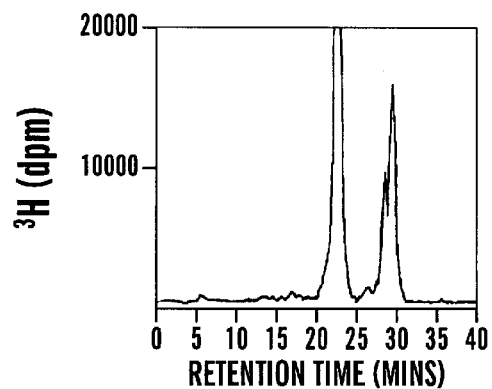

Subcellular fractionation of Sf-21 cells by sonication and centrifugation revealed retinol dehydratase activity in the 100,000×g supernatant fraction, as shown in FIG. 1C, while no activity was observed in membrane fractions, as shown in FIG. 1D. Enzyme activity was lost following dialysis of the supernatant against 20 mM Tris Cl pH 7.5/150 mM NaCl buffer (MW cutoff. 3000 Daltons), as shown in FIG. 1E, but could be restored by supplementing incubations with cytosol from either Sf-9 cells, as shown in FIG. 1F, or heat inactivated Sf-21 cells implying a requirement for a small dialyzable cofactor.

Example 2
Retinol Dehydratase Assay

20–50 μl aliquots of supernatant/column fractions were incubated with 1 μCi of [$^3$H]-retinol and 20 μl of high speed supernatant from sonicated Sf-9 cells in 200 μl assay buffer (20 mM Tris.Cl pH 7.5, 150 mM NaCl, I mM MgCl$_2$) for 15–60 minutes at 24° C. For purified recombinant enzyme, Sf-9 supernatant was omitted and replaced by 2 μM 3'-phosphoadenosine 5'-phosphosulfate ("PAPS"). Samples were delipidated and [$^3$H]-AR production quantified by a liquid scintillation radiomatic detector in series with HPLC gradient elution (20 mM Tris pH 7.4/methanol/chloroform) from a C-18 Reverse Phase 201TP54 column (Vydac, Separations Group, Hesperia, Calif.) as described by McClean et al., *Clin. Chem.*, 28:693–96 (1982) and Derguini et al., *Angew. Che. Int. Ed. Engl.*, 33:1839–41 (1994), which are hereby incorporated by reference.

Example 3
Retinol Dehydratase Purification

Figure 2:
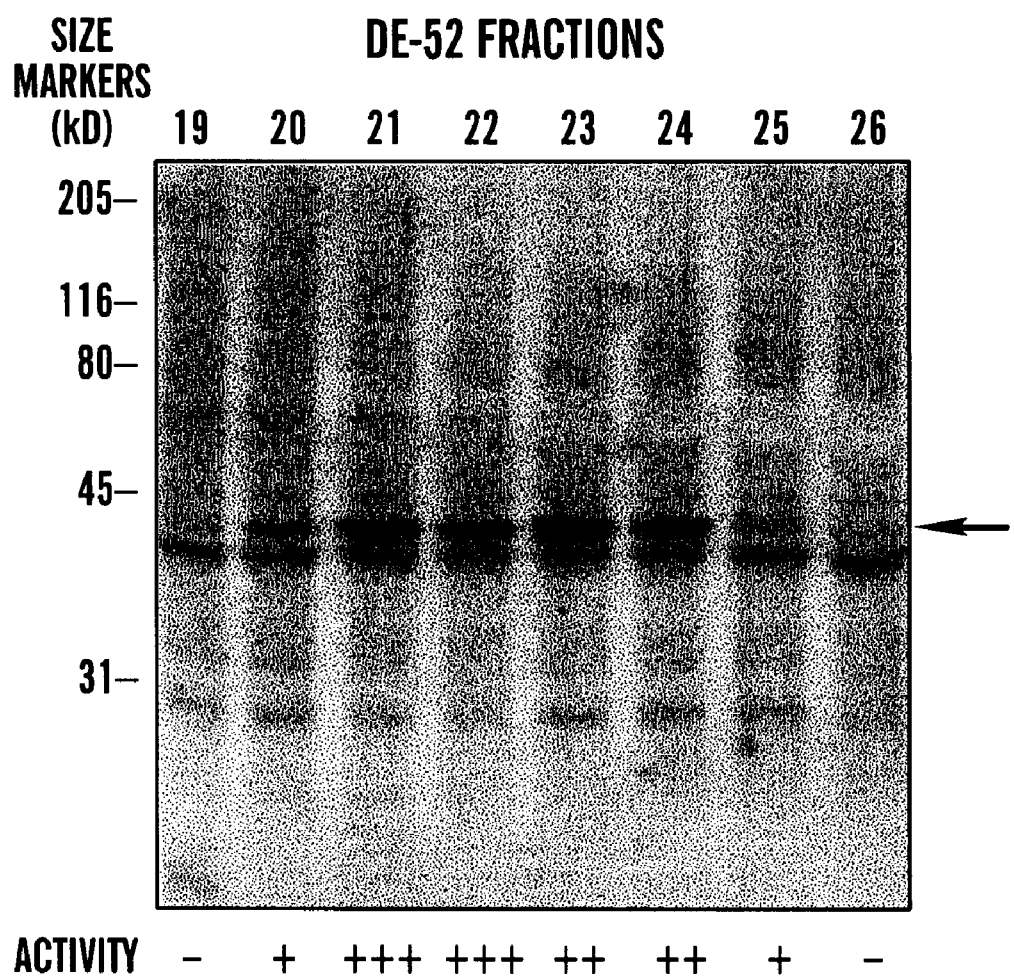
FIG. 2 is an SDS-PAGE analysis of DE-52 chromatography fractions with retinol dehydratase activity. The protein band (p41) eluting with an apparent size of 41 kD in fractions #20–24 (arrow) was correlated with the retinol dehydratase activity profile. Proteins were visualized by silver-staining.

Sf-21 cells (10 g cell pellet) were grown in Grace's insect medium supplemented with 7% fetal calf serum, harvested by centrifugation, washed, and sonicated to yield >95% lysis in the presence of protease inhibitors. Cellular debris was removed by centrifugation (10,000×g for 10 minutes) and a high speed ("HS") supernatant (100,000×g for 60 minutes) prepared. The HS supernatant (20 ml) was applied to an Ultrogel AcA54 gel filtration column (LKB, Rockland, Md.) (4×100 cm; flow rate 0.6 ml/minute 20 mM Tris.Cl, pH 7.5; fraction volume 7 ml). Fractions with retinol dehydratase activity corresponding to an apparent size of 35–45 kD were pooled and applied in 1.5M NH$_4$SO$_4$ to a HIC Econopak cartridge column (BioRad Laboratories, Melville, N.Y.) (5 ml bed volume; flow rate 1 ml/minute 20 mM Tris. Cl, pH 7.5; linear gradient 1.5–0M NH$_4$SO$_4$ in 50 minutes). Active fractions between 0.7–0.4M $NH_4SO_4$ were dialysed overnight against 20 mM Tris.Cl pH 7.5 and applied to a MonoQ Econopak cartridge column (BioRad) (5 ml bed volume; flow rate 1 ml/minute 20 mM Tris.Cl pH 7.5; linear gradient 0–1M NaCl in 60 minutes). Active fractions eluting between 0.2–0.3M NaCl were diluted 10-fold with distilled water and loaded onto a DEAE-52 column (Waters, Bedford, Mass.) (1×5 cm; flow rate 1 ml/minute 20 mM Tris.Cl pH 7.5; linear gradients of 0–0.1M NaCl in 5 minutes, 0.1–0.2M in 35 minutes, 0.2–1.0M in 5 minutes). Fractions eluting at 0.125M NaCl (#20 through 25, FIG. 2) had significant retinol dehydratase activity. Protein concentraion in column elutes were determined by continuous measurement of absorbance at 280 nm. During purification, enzyme activity was monitored by quantitation of [$^3$H]-AR production (Example 2) in the presence of Sf-9 cytosolic factor. The final enrichment of the enzyme activity from Sf-21 cell sonicates was 11700-fold.

Example 4
Retinol Dehydratase Activity

Retinol dehydratase activity was assayed in 40 μl aliquots from DE-52 chromatography fractions and compared to aliquots (10 μl per lane) analyzed on SDS-PAGE (10% polyacrylamide, reducing conditions). The protein band (p4l) eluting with an apparent size of 41 kD in fractions #20–24 (FIG. 2, arrow) was electroblotted onto a nitrocellulose membrane and correlated with the retinol dehydratase activity profile. Proteins were visualized by silver-staining.

Example 5
Expression Of Purified Recombinant Retinol Dehydratase

Figure 3A:
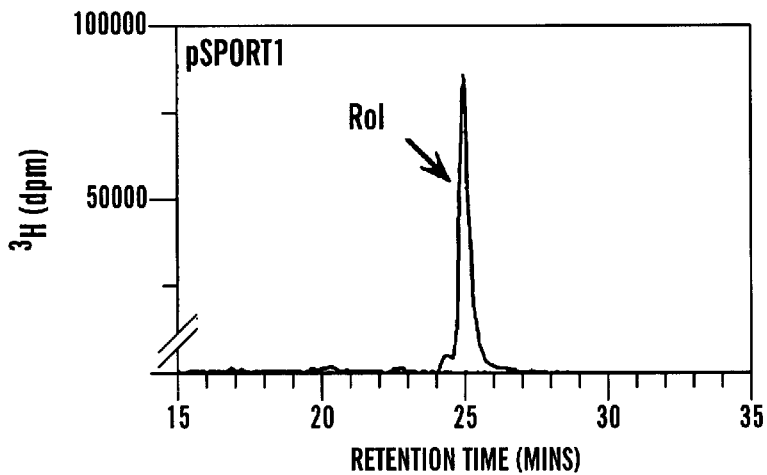
FIGS. 3A and 3B show expression of active purified recombinant retinol dehydratase ((A) shows retinol dehydratase activity in the form of graphs of crude sonicated lysates of DH5aF'lQ cultures transformed with clone pSPORT1-RDHYDRT.61 and with pSPORT1 alone; (B) SDS-polyacrylamide gel ("SDS-PAGE") (10% polyacrylamide; reducing conditions) of active recombinant retinol dehydratase (arrow) purified by HisTag affinity chromatography from clone pET15b-RDHYDRT.61 expressed in BL21pLysS (lane 1); and (B) Protein size markers (lane 2). Proteins were visualized by silver-staining.
Figure 3B:
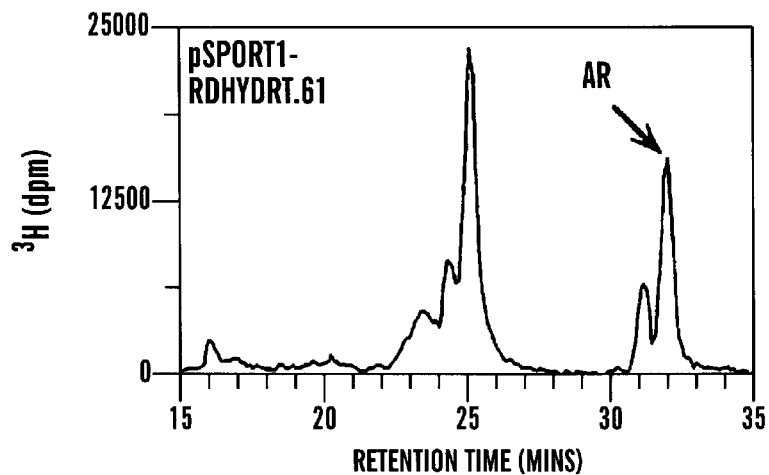
Figure 3C:
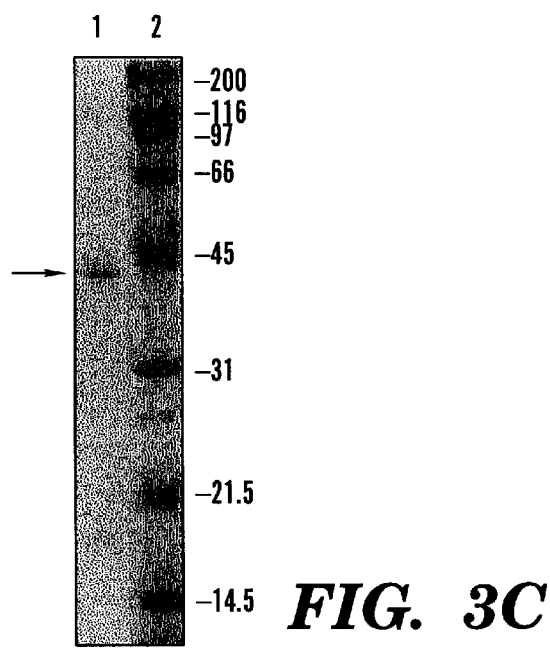

Crude sonicated lysates of DH5aF'1Q cultures transformed with clone pSPORT1-RDHYDRT.61 showed retinol dehydratase activity. In contrast, no activity was detected in cultures transformed with pSPORT1 alone. SDS-PAGE (10% polyacrylamide; reducing conditions) of active recombinant retinol dehydratase (FIG. 3, arrow) were purified (FIG. 3B) by HisTag affinity chromatography from clone pET15b-RDYHDRT.61 and expressed in BL21pLysS (FIG. 3, lane 1). Proteins were visualized by silver-staining.

Amino acid sequence information was obtained on three selected purified tryptic peptides (T34, T56, and T66; see also FIG. 4) of p4l. Degenerate oligonucleotide primers to T34 and T66 were used to generate a 212 bp specific PCR Sf-21 cDNA probe for screening of an Sf-21 cDNA plasmid library. Four independent full length clones (greater than 1500 bp) identified by DNA hybridization encoded the same 352 amino acid residue protein (MW 41.5 kDa), which, when expressed in crude bacterial lysates, had retinol dehydratase activity (FIG. 3A). Recombinant retinol dehydratase was subsequently expressed and purified using an HisTag fusion vector system (FIG. 3B).

Example 6
cDNA And Deduced Amino Acid Sequence cDNA clone RDHYDRT.61 (1564 bp) encoded an ORF for full length retinol dehydratase (1056 bp; 352 amino acid residues; 41.5 kDa). Bracketed residues (FIG. 4) represent tryptic peptides T34 (A-K: res. 26–37), T66 (S-K: res. 74–96), and T56 (Y-P: res. 103–125) for which amino acid sequence data was obtained. Highly conserved sulfotransferase sequence motifs, as described in Komatsu et al., *Biochemical and Biophysical Research Communications*, 204:1178–85 (1994) and Zheng et al., *J. Biol. Chem.*, 269:30313–19 (1994), which are hereby incorporated by reference, implicated for a PAPS binding site are underlined.

The predicted amino acid sequence (FIG. 4) displays homology to the sulfotransferases (overall 20–26% amino acid homology; 35% for a contiguous 200 amino acid C-terminal region). Sulfotransferases transfer sulfonate ($SO_3$—) groups from the universal active sulfate donor PAPS to acceptor alcohol or amine functional groups. Subsequently, it was tested whether PAPS represented the dialyzable, heat-stable factor present in cytosol needed for activity. Using purified recombinant retinol dehydratase, it was determined that PAPS was necessary and sufficient to restore activity ($k_m$=0.26±0.05 μM; n=3) in the [$^3$H]-retinol assay whereas adenosine 5'-phosphosulfate ("LAPS"), the biosynthetic precursor of PAPS, was not active in the concentration range tested (1–10 μM). The reaction mechanism for retinol dehydratase probably proceeds via the sulfated intermediate, retinyl sulfate.

Example 7
Retinol Kinetics For Retinol Dehydratase

Kinetic studies were performed with native retinol dehydratase (0.1 μg/assay) and $^3$H-retinol in the presence of constant substrate carrier protein concentrations, either delipidated BSA or recombinant cellular retinol binding protein ("CRBP"). The initial rate of AR synthesis at different substrate concentrations was determined by radiomatic detection of $^3$H-AR after HPLC separation. Plotting $V_m$ versus [S], data from a representative experiment (closed circles) were analyzed by non-linear regression (solid line) using the computer program k.cat (BioMetallics Inc., Princeton, N.J.) to derive values of $V_{max}$ (530 pmoles mg$^{-1}$ min$^{-1}$) and $k_m$ (0.66 nM). See FIG. 5A. Conversion of $^3$H-retinol was less than 10% of the total at the end point of each assay. The concentration of free retinol present in each assay was calculated based on published values for the dissociation constant of the relevant carrier protein (BSA $K_d$=1×10$^{-6}$M; CRBP $K_d$=1.2×10$^{-8}$M).

Figure 5A:
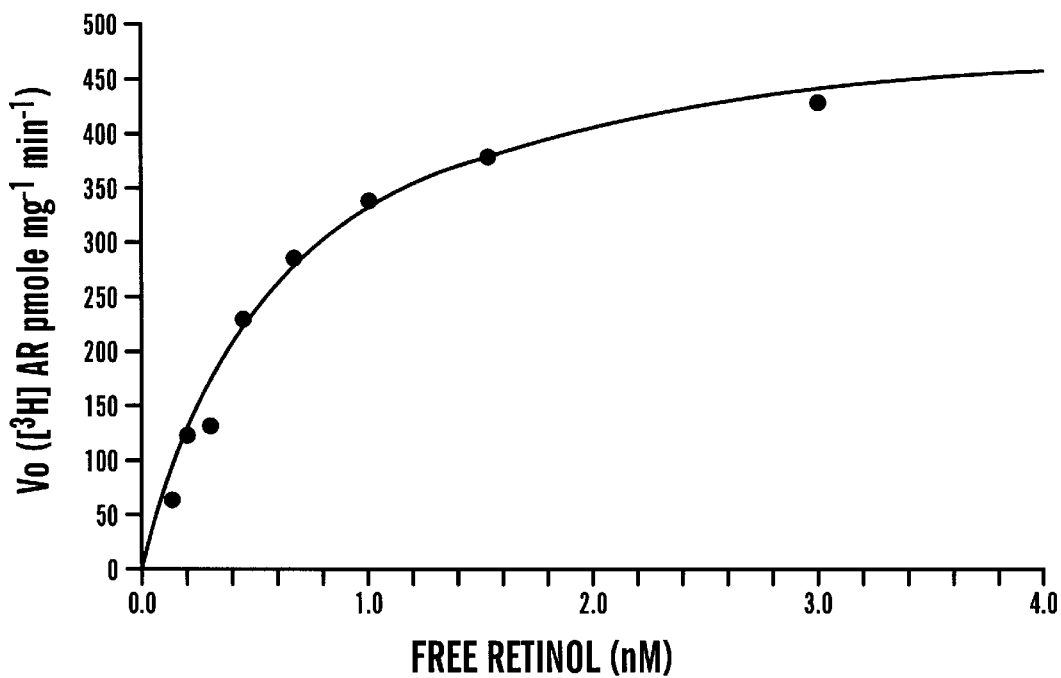
FIG. 5(A) shows kinetic studies performed with native retinol dehydratase (0.1 $\mu$g/assay) and $^3$H-retinol in the presence of constant substrate carrier protein concentrations, either delipidated bovine serum albumin ("BSA") or recombinant cellular retinol binding protein ("CRBP") (Plotting $V_o$ v. [S], data from a representative experiment (closed circles) were analyzed by non-linear regression (solid line) using the computer program k.cat (Biometallics Inc., NJ) to derive values of $V_{max}$ (530 pmoles mg$^{-1}$ min$^{-1}$) and k$_m$ (0.66 nM)).

Retinol dehydratase was inhibited by the product anhydroretinol. At a ratio of 50:1 for anhydroretinol to retinol, the reaction rate was halved. The $k_m$ for retinol was determined by kinetic analyses, as shown in FIG. 5A, performed with purified natural retinol dehydratase and confirmed with recombinant enzyme. Bacterially expressed recombinant enzyme typically gave only 10% of $V_{max}$ as compared to the native enzyme purified from Sf-21. This observation correlates well with direct binding data that indicated the recombinant enzyme had only 7% high affinity binding sites per molecule.

Carrier protein for retinol (delipidated bovine serum albumin or recombinant human CRBP) was added to reduce nonspecific binding and micelle formation. All assays gave a $V_{max}$ of 490±50 pmoles AR min$^{-1}$ enzyme (n=5), but the $k_m$ for retinol varied between assays containing different carrier proteins when the total retinol present in the system was used as the nominal substrate concentration ($k_m$ was 4×10$^{-7}$M with 10$^{-3}$M BSA, 5×10$^{-8}$M BSA, and 2.5×10$^{-8}$M with 2×10$^{-7}$M CRBP-1). However, recalculating the $k_m$ values in reference to the free retinol concentration present in the reaction mixture obtained from the respective binding affinities of carrier proteins (i.e. BSA $k_d$=1×10$^{-6}$M for retinol [Noy et al., *Biochem.*, 29:3878–83 (1990), which is hereby incorporated by reference]; CRBP-1 $k_d$=1.2×10$^{-8}$M for retinol (Ong et al., *Methods Enzymol.*, 67:288–96 (1980), which is hereby incorporated by reference) gave a consistent average $k_m$ for retinol of 1.0×10$^{-9}$M (range 0.6–2.0×10$^{-9}$M, n=5).

Example 8
Fluorimetric Titration for Retinol Dehydratase

Figure 5B:
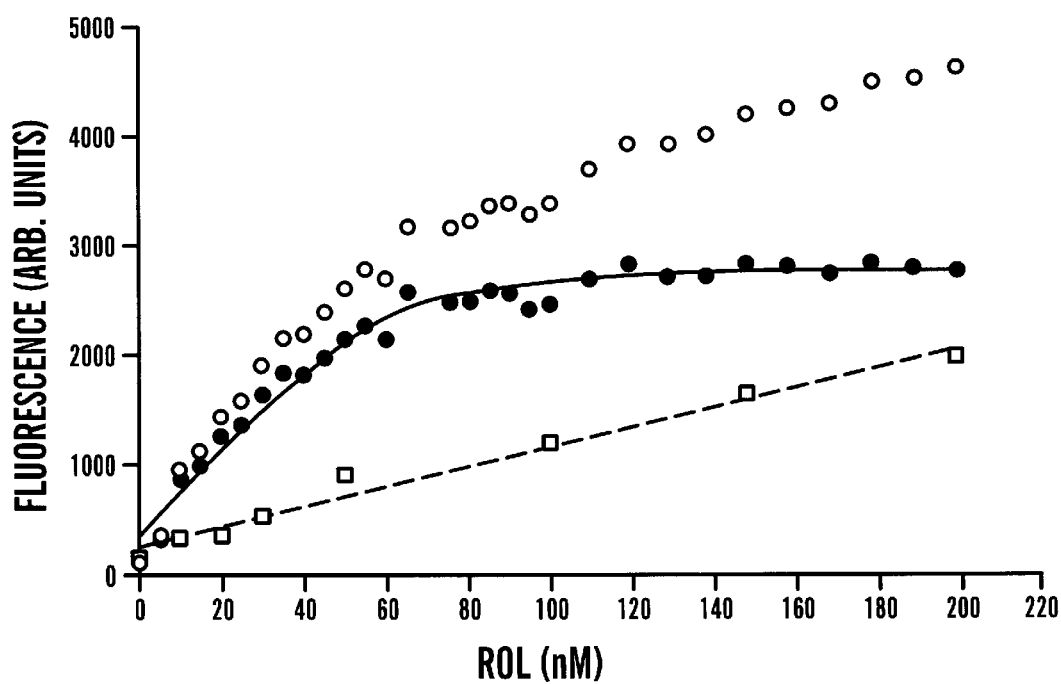
FIG. 5(B) shows recombinant retinol dehydratase (1 $\mu$M) titrated with retinol from a concentrated solution in ethanol (final ethanol concentration <2.0%). Binding was monitored by following the fluorescence enhancement of retinol (excitation—330 nm; emission—480 nm, open circles). The fluorescence contribution of free retinol was determined by titration with retinol in the absence of protein (open squares), analyzed by linear regression analysis (dashed line) and subtracted from the titration data to give the corrected titration binding curve (closed circles). The data were fitted (solid line) using an equation derived from simple binding theory.

The extremely low $k_m$ value for retinol suggested a high affinity interaction between enzyme and substrate. Direct binding experiments were, therefore, performed with recombinant enzyme by fluorescence titrations in the absence of cofactor, i.e. under conditions that do not allow catalysis (FIG. 5B). Retinol is an efficient fluorophore and its interactions with proteins are often accompanied by a marked increase in its fluorescence. This phenomenon reflects movement of retinol from the aqueous solution to a less polar and more restrictive environment within a protein binding site, and has been extensively used to monitor the binding of retinol to binding proteins, as described by Cogan et al., *Eur. J. Biochem.*, 65:71–75 (1976); Ong et al., *J. Biol Chem.*, 253:828–32 (1978); and Noy et al., *Biochemistry*, 30:6380–86 (1991), which are hereby incorporated by reference.

Recombinant retinol dehydratase (1 $\mu$M) was titrated with retinol from a concentrated solution in ethanol (final ethanol concentration <2.0%). Binding was monitored by following the fluorescence enhancement of retinol (excitation—330 nm; emission—480 nm, open circles). See FIG. 5B. The fluorescence contribution of free retinol was determined by titration with retinol in the absence of protein (FIG. 5B, open squares), analysed by linear regression analysis (FIG. 5B, dashed line) and subtracted from the titration data to give the corrected titration binding curve (FIG. 5B, closed circles). The data were fitted (FIG. 5B, solid line) using an equation derived from simple binding theory as described in Norris et al., *Biochim Bioshys Acta*, 1209:10–8 (1994), which is hereby incorporated by reference, to yield the number of binding sites (8%) and the equilibrium dissociation constant ($K_d$=9 nM).

Titration curves indicated the presence of 0.07 (range 0.06–0.08, n=3) binding sites and an equilibrium dissociation constant ($K_d$) of 9 (range 2.0–15.0 nM, n=3) Since measurements at low protein concentrations were technically difficult, protein concentrations significantly higher than the $K_d$ (between 0.5–1 $\mu$M) were used. The derived $K_d$ should thus be considered an upper limit for the actual value. Nevertheless, it agreed with the $K_m$, confirming retinol dehydratase has a high affinity binding site for free retinol. These data also indicate that high affinity binding of retinol to the enzyme does not require the presence of the cofactor PAPS.

Due to its lipophilic nature, retinol partitions in vivo predominantly between membranes and specific binding proteins. Under normal conditions where retinol saturates high affinity binding proteins, the cytosolic concentration of free retinol was determined by the cellular level of holo-CRBP complex as described in Noy et al., *Biochem.*, 30:6380–86 (1991), which is hereby incorporated by reference. Since the experimentally determined $K_d$ for the dehydratase/retinol complex was lower than the reported $K_d$ for the complex of retinol to CRBP as described in Ong et al., *Methods Enzymol.*, 67:288–96 (1980), which is hereby incorporated by reference, the cytosolic concentration of free retinol will exceed that required for full activation of insect retinol dehydratase (or a mammalian homolog with similar kinetic parameters).

As described above, the amino acid sequence of retinol dehydratase was found to be homologous to the sulfotransferases and used the same co-substrate, PAPS. Distinct sulfotransferases are required for the sulfation of biological molecules such as steroid hormones, thyroid hormones, monoamine neurotransmitters and alcohols as described in R., Hobkirk, *Can. J. Biochem. Cell Biol.*, 63:1127–44 (1985), which is hereby incorporated by reference. Sulfation of these signalling molecules has been postulated to be a m echanism for the regulation of activity in physiological processes including growth, differentiation, and development as described in Coughtrie et al., *Chemico-Biological Interactions*, 92:247–56 (1994), which is hereby incorporated by reference. The conversion of growth supportive retinol to the growth suppressive anhydroretinol via sulfate mediated catalysis further exemplifies this conservation of principle between isoprenoid-derived signalling mole cules and the enzymes (specifically sulfotransferases) that manipulate them. Retinol dehydratase represents the prototypic experimental system for studying how a cytosolic retinol utilizing enzyme may regulate local levels of "vitamin A activity" in target cells and tissues.

Example 9

Activation of Resting Fibroblasts

Figure 6A:
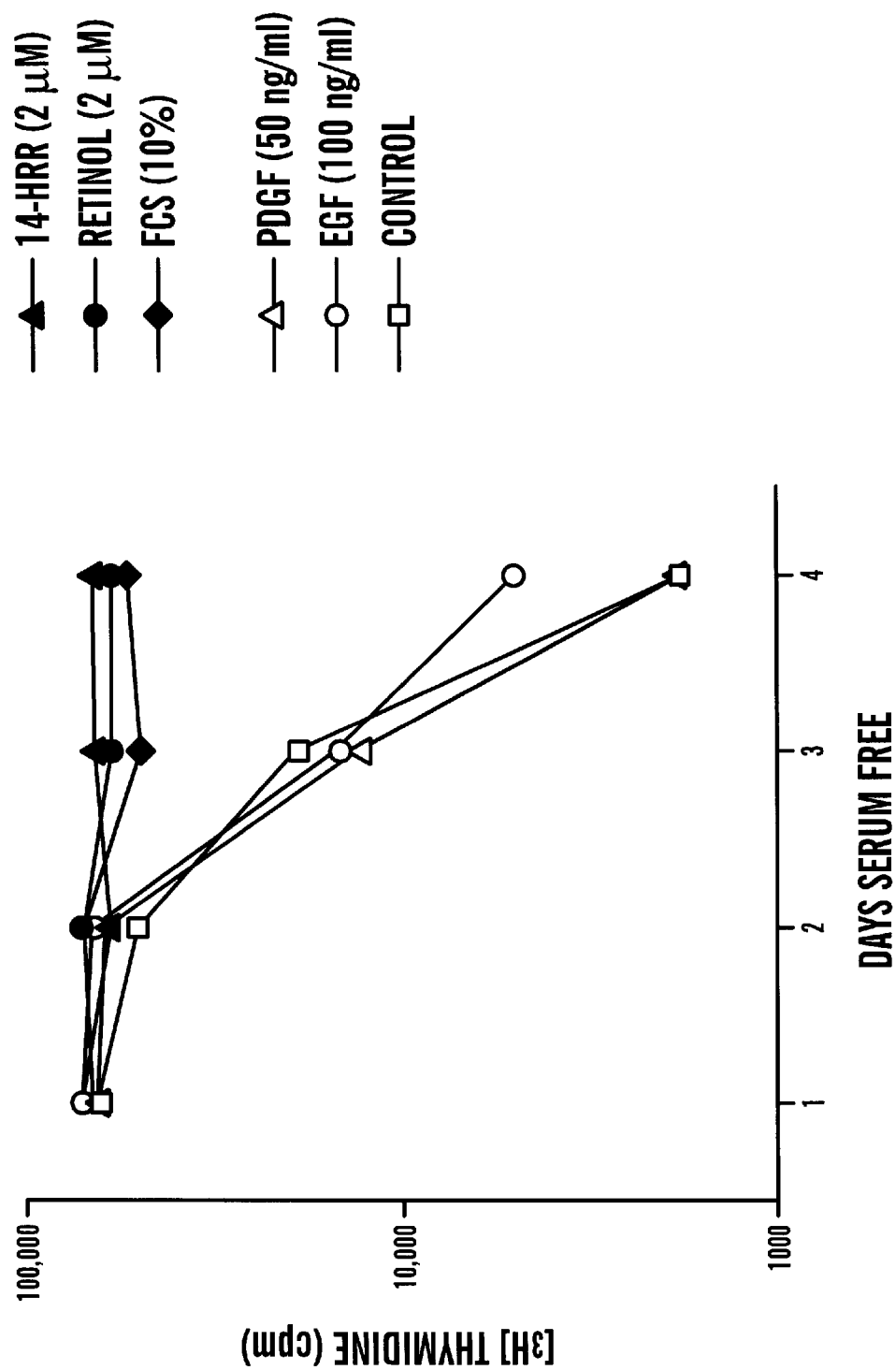
FIGS. 6A and 6B show the activation of resting NIH 3T3 cells.

Confluent NIH 3T3 cells were starved for 1 to 4 days in medium containing 0.1% serum. Then, these starved cells were treated with serum, PDGF, EGF, retinol, or 14-HRR. Activation was quantitated by measuring the [$^3$H] thymidine incorporated into newly synthesized DNA during the subsequent 24 hours (FIG. 6A). After a single day of serum starvation, the cells were not yet arrested, and the control cells incorporated the same amount of thymidine as the treated cells. After 2 days of serum deprivation, untreated cells incorporated slightly less thymidine, while cells treated with serum, peptide growth factors and retinoids maintained the original level of thymidine incorporation. In contrast, cells deprived of serum for 3 or 4 days were fully growth arrested; untreated cells incorporated little or no thymidine. Serum reversed this growth arrest, while PDGF and EGF had no effect. Retinol and 14-HRR, substituted for serum, activated the cells at least as well as serum. All subsequent activation experiments were conducted using 4 day starved NIH 3T3 cells.

Figure 6B:
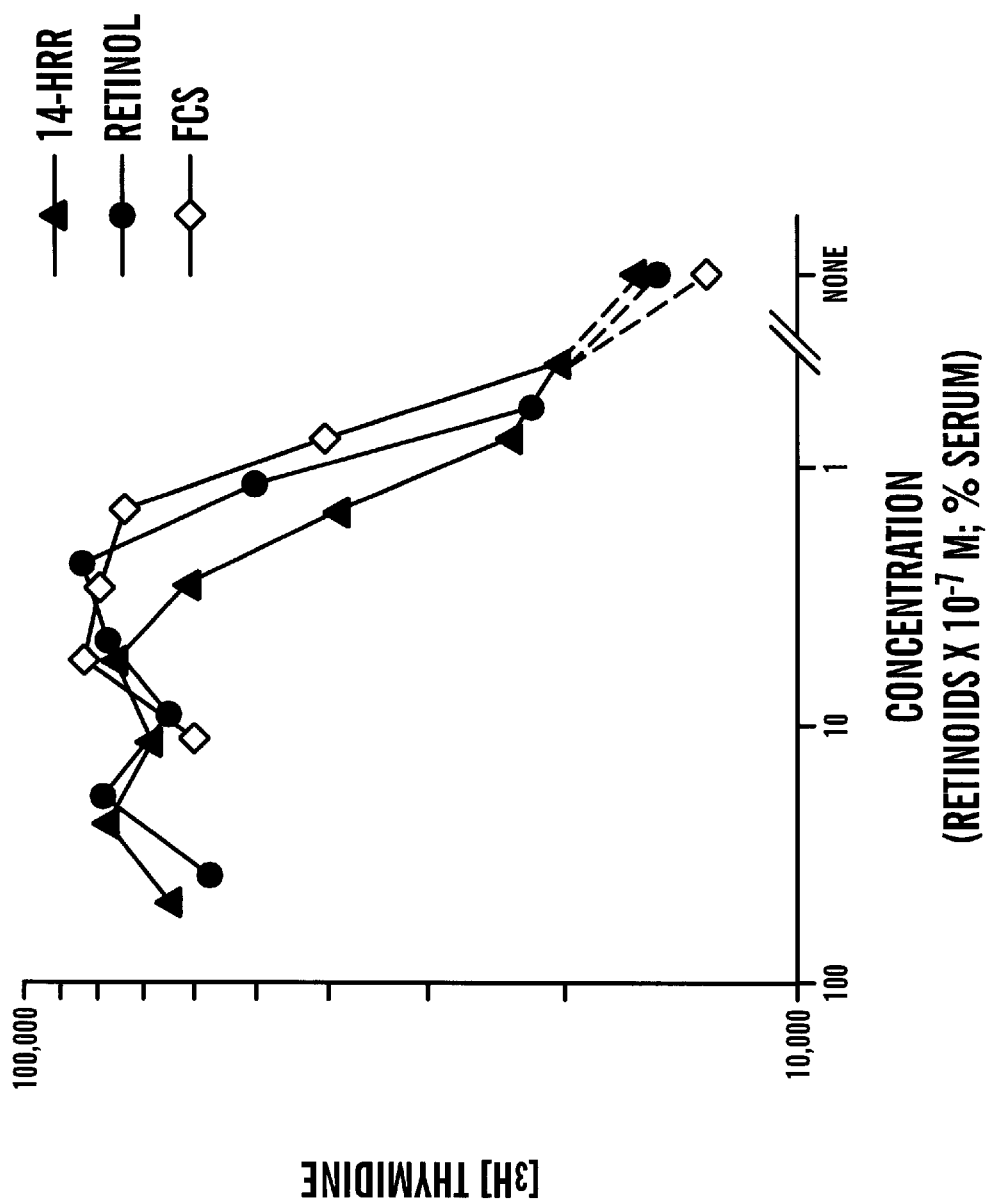

Typical dose-response curves of fetal calf serum, retinol, and 14-HRR are shown in FIG. 6B. Retinol and 14-HRR activate resting 3T3 cells at submicromolar concentrations. Insulin (present at 5 $\mu$g/ml in the defined medium used) did not activate resting 3T3 cells but, in combination with serum or retinoids, potentiated thymidine uptake 1.5 to 2 fold (data not shown). PDGF ($\leq$1000 ng/ml), EGF ($\leq$500 ng/ml), retinoic acid ($\leq$5 $\mu$M), phorbol ester ($\leq$1 $\mu$M), and sphingosine derivations ($\leq$100 $\mu$M) were unable to activate resting cells under the conditions tested.

Since serum contains retinol, starvation in medium containing only 0.1% serum could decrease intracellular levels of retinol. Eppinger, et al., *J. Exp. Med.*, 178:1995–2005 (1993), which is hereby incorporated by reference. The decrease of cellular retinol concentration was measured over time. After 3 days, when retinol is necessary for 3T3 cells to become activated, the cellular retinol levels have decreased from 0.1 $\mu$M to below 0.03 $\mu$M. The decrease of cellular retinol levels may directly correlate with the growth arrest.

No difference was observed in the time course of cells entering the S phase of the cell cycle when serum-starved resting cells were activated with serum, retinol, or 14-HRR; synchronized NIH 3T3 cells needed 16 h from the start of activation to entry of the S phase (FIG. 7). PDGF, EGF, and PMA treated NIH 3T3 cells did not enter the S phase (data not shown).

Figure 8:
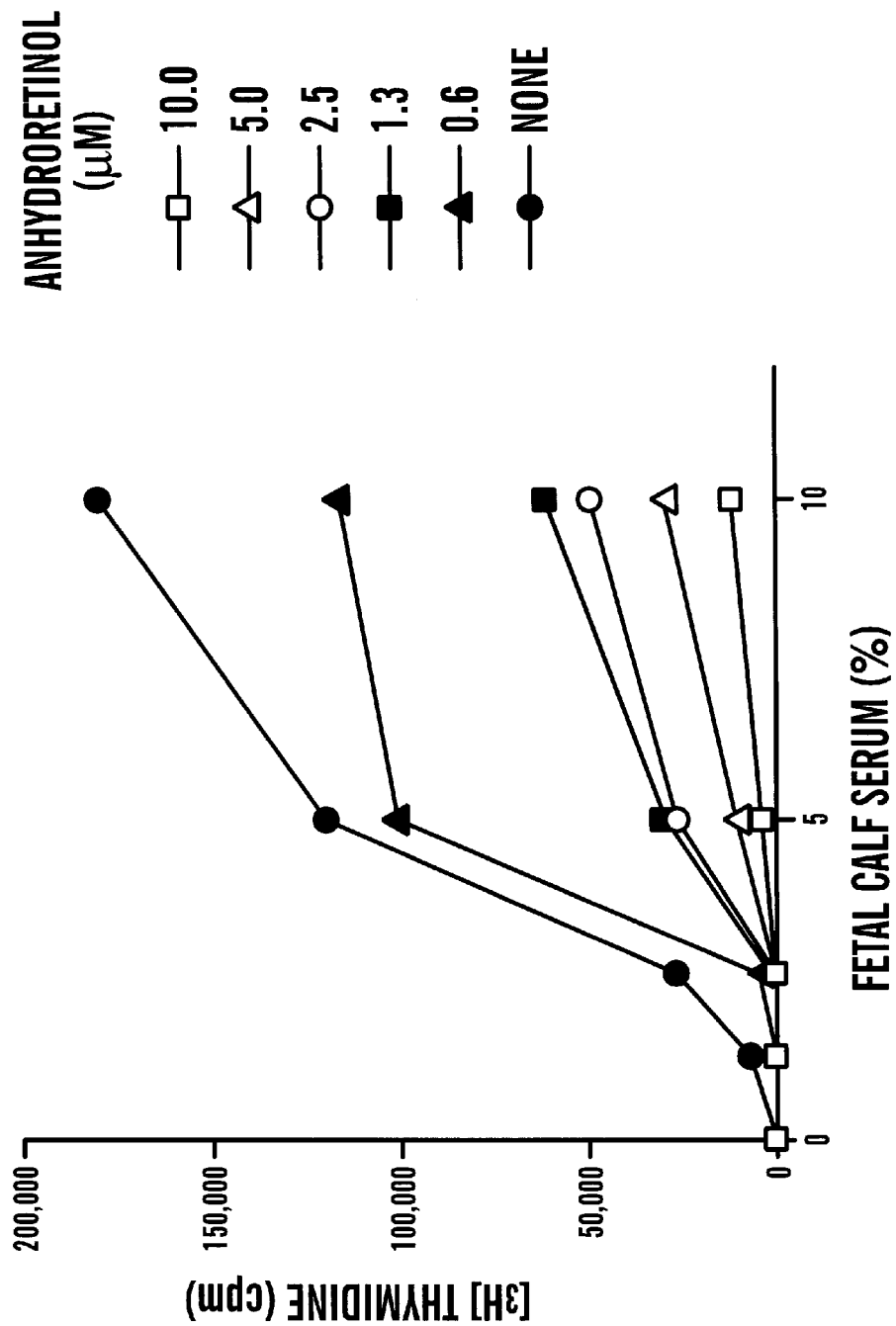
FIG. 8 shows that anhydroretinol competitively inhibits the activation of 3T3 cells by serum. Cells starved for 4 days in DMEM/0.1% fetal calf serum were activated in 100 $\mu$l/well ITLB medium. At the indicated time points, anhydroretinol was added in 100 $\mu$l ITLB medium. This method is described in FIG. 6. The data in FIG. 8 represents the mean of quadruplicate measurements and SDs were $\leq$20%.

Anhydroretinol is a physiological retinol derivative which competitively inhibits retinol and 14-HRR supported lymphocyte and HL-60 cell growth. Eppinger, et al., *J. Exp. Med.*, 178:1995–2005 (1993) and Buck, et al., *J. Exp. Med.*, 178:675–80 (1993), which are hereby incorporated by reference. The same anhydroretinol effect is seen in 3T3 cells; anhydroretinol competitively inhibits activation by retinol and 14-HRR. Furthermore, anhydroretinol blocks activation by serum in a dose-dependent manner (FIG. 8). Thus, retinol in serum is at least one of the essential components in serum-induced 3T3 cell activation.

Figure 9A:
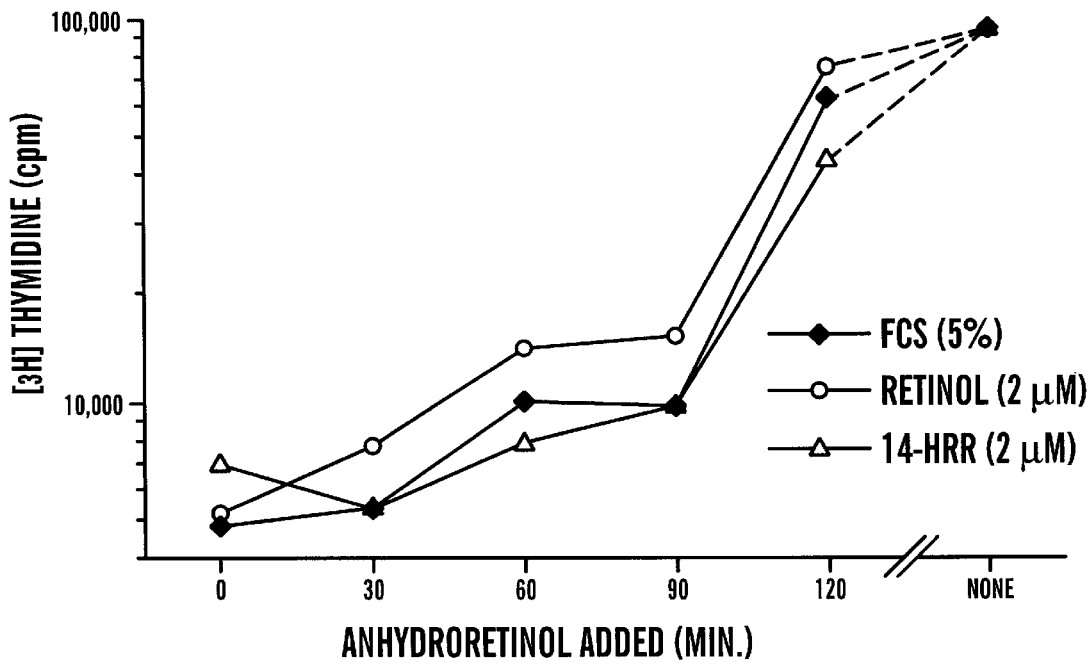
FIG. 9 shows that anhydroretinol blocks 3T3 cell activation during the first 90 minutes. Cells starved for 4 days in DMEM/0.1% fetal calf serum were activated with 5% fetal calf serum, 2 $\mu$M retinol, or 2 $\mu$M 14-HRR. At the time points, $10^{-5}$M anhydroretinol was added. The cumulative [$^3$H]thymidine incorporation was determined after 24 hours. The insert shows the same time course covering the full 24 hour period. The method is described in FIG. 6. The data in FIG. 9 represents the mean of triplicate measurements and SDs were ≦20%.
Figure 9B:
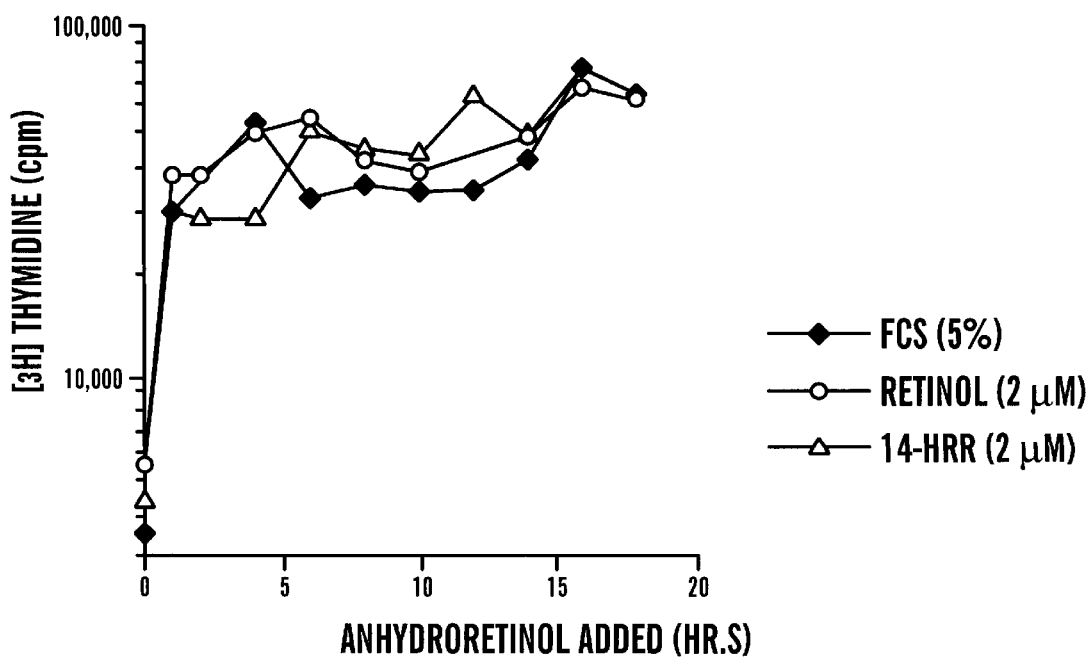

Additionally, anhydroretinol was used to determine the time period during which retinoids are needed for the activation of quiescent 3T3 cells. Anhydroretinol prevented the activation of resting NIH 3T3 cells by both retinoids and serum if applied within 90 min of activation. After 2 hours, anhydroretinol was unable to block activation, and the cells were committed to enter the S phase (FIG. 9).

The pair of retro-retinoids, anhydroretinol and 14-HRR, exist in evolutionarily distant species, e.g. mammals and insects. Derguini, et al., Angew. Chem. Int. Ed. Engl., 33:1839–41 (1994), which is hereby incorporated by reference. It has been demonstrated that retinol and 14-HRR are the first examples of small lipophilic molecules able fully to replace serum in 3T3 cell activation. The competitive inhibition of serum activation by anhydroretinol suggests that retinol is one of the essential components in serum. Since retinol in serum is metabolized to 14-HRR in cycling 3T3 cells and 14-HRR activation can also be blocked by anhydroretinol, 14-HRR is likely a downstream mediator of activation by serum. In tissues where micromolar concentrations of anhydroretinol are present, e.g. liver and lung, anhydroretinol may act physiologically to prevent the activation of quiescent cells. These results imply the existence of an intracellular signaling pathway of vitamin A action distinct from that of retinoic acid.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding retinol dehydratase, wherein the DNA molecule (1) encodes an amino acid molecule which comprises the amino acid sequence of SEQ. ID. No. 2 or (2) hybridizes at 40° C. in 2×SSC and 40% formamide to a nucleic acid molecule comprising the nucleotide sequence of SEQ. ID. No. 1.

2. An isolated DNA molecule according to claim 1, wherein the retinol dehydratase has an amino acid sequence corresponding to SEQ. ID. No. 2.

3. An isolated DNA molecule according to claim 2, wherein said DNA molecule has a nucleotide sequence corresponding to SEQ. ID. No. 1.

4. An isolated DNA molecule according to claim 1, wherein the retinal dehydratase has a molecular weight of about 41 to 42 kDa.

5. An isolated DNA molecule according to claim 1, wherein the retinol has a $K_m$ value from about $0.6 \times 10^{-9}$ to $2.0 \times 10^{-9}$ M.

6. A recombinant DNA expression system comprising an expression vector into which is inserted the heterologous DNA molecule according to claim 1.

7. A recombinant DNA expression system according to claim 6, wherein the heterologous DNA molecule has a nucleotide sequence corresponding to SEQ. ID. NO. 1.

8. A recombinant DNA expression system according to claim 6, wherein the heterologous DNA molecule is inserted into said vector in proper sense orientation and correct reading frame.

9. A recombinant DNA expression system according to claim 6, wherein the expression vector is selected from the group consisting of a plasmid, a virus, and a bacteriophage.

10. A host cell incorporating a heterologous DNA according to claim 1.

11. A host cell according to claim 10, wherein said heterologous DNA has a nucleotide sequence corresponding to SEQ. ID. NO. 1.

12. A host cell transformed with the recombinant DNA expression system according to claim 6.

* * * * *